United States Patent
Sharma et al.

(10) Patent No.: US 11,634,684 B2
(45) Date of Patent: Apr. 25, 2023

(54) INTEGRATED PROCESS FOR ETHANOL SEPARATION FROM FERMENTED BROTH FOR LOW TEMPERATURE APPLICATIONS

(71) Applicant: Indian Oil Corporation Limited, Mumbai (IN)

(72) Inventors: Mukesh Kumar Sharma, New Delhi (IN); Gaurav Bajaj, New Delhi (IN); Alok Sharma, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 505 days.

(21) Appl. No.: 16/778,848

(22) Filed: Jan. 31, 2020

(65) Prior Publication Data

US 2020/0325438 A1    Oct. 15, 2020

(30) Foreign Application Priority Data

Apr. 9, 2019    (IN) .............................. 201921014261

(51) Int. Cl.
*C12M 1/00* (2006.01)
*C07C 29/78* (2006.01)
*C07C 29/80* (2006.01)

(52) U.S. Cl.
CPC .............. *C12M 47/10* (2013.01); *C07C 29/78* (2013.01); *C07C 29/80* (2013.01); *C12M 21/12* (2013.01); *C12M 29/00* (2013.01)

(58) Field of Classification Search
CPC ...... C12M 47/10; C12M 21/12; C12M 29/00; C07C 29/78; C07C 29/80
USPC ........................................................ 435/162
See application file for complete search history.

(56) References Cited

U.S. PATENT DOCUMENTS

| 4,428,799 A * | 1/1984 | Standiford ............. B01D 3/001 159/24.3 |
| 4,952,503 A | 8/1990 | Granstedt |
| 8,535,413 B2 | 9/2013 | Bryan et al. |
| 9,308,469 B2 | 4/2016 | Kiuchi et al. |
| 2007/0031954 A1 | 2/2007 | Mairal et al. |
| 2009/0215139 A1* | 8/2009 | Datta ....................... C12P 7/065 435/162 |
| 2010/0099155 A1* | 4/2010 | Frank ....................... C12M 47/10 435/150 |
| 2013/0015052 A1 | 1/2013 | Vane et al. |
| 2013/0175158 A1 | 7/2013 | Kiuchi et al. |
| 2018/0290073 A1 | 10/2018 | Brown et al. |

FOREIGN PATENT DOCUMENTS

| CN | 1006902 B | 2/1990 |
| JP | S60209202 A | 10/1985 |
| WO | 2007088767 A1 | 6/2009 |
| WO | 2011017744 A1 | 2/2011 |
| WO | 2011103277 A1 | 8/2011 |
| WO | 2012153523 A1 | 11/2012 |
| WO | 2018187073 A1 | 10/2018 |

OTHER PUBLICATIONS

Japanese Office Action, dated Feb. 15, 2021, from Japanese Patent Application No. 2020-014277 filed Jan. 31, 2020.
India Examination Report, dated Aug. 5, 2021, from India Patent Application No. 201921014261 filed Apr. 9, 2019.

* cited by examiner

*Primary Examiner* — Jennifer M. H. Tichy
(74) *Attorney, Agent, or Firm* — Workman Nydegger

(57) ABSTRACT

The present invention provides to a process for recovery of an organic compound (i.e. Ethanol, propanol, butanol, Acetone, iso-propyl alcohol) from a fermented broth which is produced from different fermentation technologies. The present invention particularly relates to an integrated process for ethanol separation from the fermentation broth using integrated vapor compressing unit (turbofans), evaporator (falling film) and a broth stripper column (vacuum distillation system). The process is operated under low temperature for the separation and recovery of the organic compound (particularly ethanol) from the fermented broth containing live microbes typically below or at 50° C. to ensure the activity of the microbes in the broth recycle. Again, the activity of the microbes is further ensured by maintaining the residence time of the microbe containing broth outside the Fermentor is less than or equal to 10 minutes.

8 Claims, 5 Drawing Sheets

INTEGRATED PROCESS FOR ETHANOL SEPARATION FROM FERMENTED BROTH FOR LOW TEMPERATURE APPLICATIONS

FIELD OF THE INVENTION

The present invention relates to an integrated process for separation of an ethanol from fermented broth for low temperature applications, wherein the fermented broth is produced from different fermentation technologies. The present invention particularly relates to an integrated process for ethanol separation from the broth produced from Gas Fermentation process using integrated vapor compressing unit (turbofans), falling film evaporator and a broth stripper column (vacuum distillation system). The present invention is equally applicable for the separation of other organic compounds i.e. propanol, butanol, acetone and iso-propyl alcohol (IPA) from the fermented broth.

BACKGROUND OF THE INVENTION

Broth from Fermentor contains Ethanol, Water, Microorganisms (Live Microbes)/biomass along with traces of other process chemicals produced by side reactions. The Ethanol has to be recovered from the Fermented Broth containing 1-5 wt % ethanol and remaining broth is recycled back to the Fermentor Section in the Fermentation process. Since the broth contains the live micro-organisms, the Ethanol Separation from Broth has to be carried out typically below 45° C. to keep the micro-organisms alive and active for the fermentation process back in the Fermentor. Further, micro-organisms are strongly dependent on feed gas for their survival; this requires minimum residence time of the broth (containing micro-organism) outside the fermentation system to ensure that the micro-organisms remain alive and active. Hence, it is challenging to design the ethanol separation system at low temperature with minimum residence time outside of the Fermentor. Additionally, in order to compete with the other available technologies, it is highly desirable to keep CAPEX & OPEX of the plant as minimum as possible while meeting the objective of ethanol separation with required condition.

Conventional 1G/2G technology for ethanol recovery are not based on the recycling of the live micro-organisms, so the ethanol separation can be performed at the distillation column temperature of about 90° C. or above using low pressure steam reboiler/direct injection. Overhead vapors are condensed and further routed to the downstream to the ethanol recovery & dehydration section for obtaining high purity ethanol. Such type of convectional schemes cannot work for the processes utilizing bio-catalyst (live microbes) for fermentation processes. Such high temperatures will lead to killing of the microbes and reduce growth/activity of microbes in the gas /bio-mass fermentation processes in upstream Fermentor. Further, in other process like membrane separation methods of ethanol recovery, a cell recycle membrane is used for separating the ethanol-water mixture from broth containing live microbes and allowing the microorganism to recycle back to fermentation process at the low temperature requirement. However, repair & maintenance cost are high for membrane separation modules. Also, very large area is required for installing such membranes especially for lower microbes growth rate depending on the feed gas constituents. Again , the reliability of membranes are poor w.r.t changes in operating condition, feed quality and any ingress of particulate matter in broth resulting in lowering of life cycle of membranes that in turn requires frequent replacement during project life.

US 2007/0031954 describes an integrated process which includes multiple membranes which include a first membrane separation, followed by dephlegmation step, and another membrane separation for ethanol dehydration. A problem with this approach is the need for solids removal from the fermentation broth before the membrane separation process. The solids removal step creates additional capital investments and operating costs which increases the overall ethanol production cost.

U.S. Ser. No. 13/809,269 utilizes the principle of low temperature broth separation achieved along with heat integration for ethanol separation suitable only for ethanol-fermented liquid generated by saccharification fermentation where the objective is to separate ethanol and also to prevent enzyme being denatured. However, the said art has heat integrated system consisting of vacuum distillation, compressor and simple heat exchanger. The enzyme rich stream is drawn from the bottom of the column. Hence the process as described by the said patent applications cannot ensure the total protection of live microbes at various operating conditions/operational disturbances during the operation of the plant.

U.S. Pat. No. 8,535,413B2 discloses a fermentation process for ethanol recovery using an integrated Mechanical Vapour Recompression (MVR) and Membrane Vapour Permeation system, wherein fermentation is carried out at a temperature in excess of 75-100° C. Further, the process discloses recovery of ethanol from a broth feed ethanol concentration higher than 5 wt %. Additionally, the process uses steam and carbon dioxide as stripping medium in an apparatus called Fermenting stripper.

US2013/0175158A1 discloses a method for producing ethanol and a device for producing ethanol that are suitable for the recycled use of an enzyme. The patent application provides a method for producing ethanol wherein the method involves purifying ethanol from an ethanol-fermented liquid generated by saccharification fermentation of a biomass starting material, while the apparatus for producing ethanol comprises of a vacuum distillation tower for distilling ethanol vapor containing water vapor, and removing as a bottom production enzyme-containing concentrated waste liquid in addition to a rectifying column configured to rectify the ethanol vapor distilled from the vacuum distillation tower.

Due to above limitations in such type of technologies for ethanol production, the ethanol separation from a fermentation broth cannot be effectively done as per the conventional process available in $1^{st}$ Generation (1G) or/$2^{nd}$ Generation (2G) technologies as well as the membrane separation method of ethanol plant. Hence, it is highly desirable to find out alternative technologies/processes/methods that can be utilized for Ethanol separation from such type of broth and which are also energy efficient. Various approaches have been or are currently being explored to find a solution to the problem of ethanol separation requirement at very low temperature with objective of protecting live microbes along with minimizing the energy consumption & CAPEX for the ethanol recovery from broth. Further, in such technologies, the microbes have to be protected in the broth solution outside of Gas Fermentor based on temperature & residence time limitation. This requires recycling back the microbes after ethanol separation from fermentation broth keeping temperature and residence time within the design limits. Although the process of ethanol separation from broth is well known for $1^{st}$ Generation (1G) or/2$^{nd}$ Generation (2G) technologies and membrane separation methodologies, study of the prior arts does not reveal any integrated process or approach that ensures effective ethanol (and other lower alcohols and lower ketones) separation from a fermentation broth containing living microbes such that the microbes are retained in the recycle broth after the separation of the ethanol.

SUMMARY OF THE INVENTION

Accordingly, the present invention provides "an integrated process" for separation of an organic compound (i.e. ethanol, propanol, butanol, acetone, iso-propyl alcohol), particularly ethanol from a fermented broth wherein the process operates at a lower system temperature & residence time ensuring maximum ethanol recovery at low temperature and retaining the activity of the micro-organism in the recycle broth for further fermentation in the gas fermentation section. The present invention overcomes the drawbacks of the prior arts and ensures maximum ethanol recovery at low temperature while ensuring the activity of the micro-organism desired for fermentation in the gas fermentation section based on the use of an integrated system comprising a broth stripper column (vacuum distillation system), falling film evaporator and a vapor compressing unit (turbofans).

The present invention provides an integrated process for separation of an organic compound from a fermented broth, the process comprising:
   (a) feeding a degassed and pre-heated fermented broth into a broth stripper column for generating a vapor;
   (b) compressing the vapor obtained from overhead of the broth stripper column in a turbofan to obtain a compressed vapor at a pressure ranging from 160 to 200 mmHg;
   (c) routing a demineralized water from bottom of the broth stripper column to a falling film evaporator to obtain a stripping steam, wherein the stripping steam is routed into the broth stripper column;
   (d) routing the compressed vapor obtained in step (b) to the falling film evaporator for heat transfer from the compressed vapor to the demineralized water for generating the stripping steam, wherein the compressed vapor is condensed to obtain a mixture of a condensed liquid and a remaining vapor;
   (e) routing the mixture of condensed liquid and remaining vapor obtained in step (d) to a broth stripper condenser for condensing the remaining vapor into a condensed liquid; and
   (f) collecting the condensed liquid obtained in step (d) and step (e) in a rectifier feed drum for distillation to obtain 15-25 wt % of the organic compound;
wherein the broth stripper column is operated at temperature ranging from 15 to 50° C. for a residence time of ranging from 1-10 minutes;
wherein the organic compound is selected from ethanol, propanol, butanol, acetone and iso-propyl alcohol.

The process described in steps (a) to (f) of the present invention is equally applicable for the separation of propanol, butanol, acetone, iso-propyl alcohol (IPA) from the fermented broth Further, the present invention provides an integrated system for separation of an organic compound from a fermented broth, wherein the organic compound is selected from ethanol, propanol, butanol, acetone, iso-propyl alcohol, the system comprising:

a broth stripper column (C-1) provided with a packed bed section packed with a mass transfer bed of packing material, a chimney tray below the packed bed section for removal of recycle broth, and a tray section at bottom for providing the demineralized water to a falling film evaporator for generation of stripping steam;
   a turbo fan (K-1) for compressing a vapor obtained from overhead of the broth stripper column;
   a falling film evaporator (E-1) for heat transfer from a compressed vapor to a demineralized water obtained from bottom of the broth stripper column (C-1) and to obtain a mixture of a condensed liquid and a remaining vapor;
   a condenser (E-3) for condensing the remaining vapor obtained from the falling film evaporator to obtain a condensed liquid ;
   a rectifier feed drum (V-2)for collecting a the condensed liquid obtained from the condenser (E-3);
   an auxiliary reboiler (E-2) for heating a bottom product from the broth stripper column with a low pressure steam during start-up operation; and
   a start-up condenser (E-5) for condensing the compressed vapor during start-up operation.

OBJECTIVES OF THE PRESENT INVENTION

The primary objective of the present invention is to recover organic compounds (i.e. ethanol, propanol, butanol, acetone, iso-propyl alcohol), particularly ethanol efficiently from the fermented broth containing live microbes while protecting microbes from temperature excursions and residence time limitation.

Another objective is to provide a low temperature separation & recovery of ethanol from the fermented broth containing live microbes at temperature typically below or at 50° C., preferably below 45° C.

Another objective of the present invention is to ensure the activity of the microbes by maintaining the residence time of the microbe containing broth outside the Fermentor as less than 10 minutes.

Yet another objective of the present invention is to provide an integrated method that performs efficiently with broth containing ethanol as low as 1 wt %.

Another objective of the present invention is to provide an integrated method of ethanol separation involving turbofans, evaporator and broth stripper column for energy optimization and lowering the OPEX (Operating Cost) of the plant.

DETAILED DESCRIPTION OF THE INVENTION

The present invention relates to an integrated process for recovery of ethanol from fermented broth which is produced from different fermentation technologies. The present invention particularly relates to an integrated process for ethanol separation from the broth produced from Gas Fermentation process using an integrated system of broth stripper column (vacuum distillation system), Turbofans and falling film evaporator.

The present invention is equally applicable for the separation of propanol, butanol, acetone, iso-propyl alcohol (IPA) from broth solution. Further, the present invention finds its application globally for separation of ethanol, acetone, iso-propyl alcohol (IPA), propanol, butanol (at low temperature) in the various fermentation technologies targeting ethanol, acetone, iso-propyl alcohol (IPA) production from the waste sources like municipality waste (MSW), industrial waste gases, refinery off gases, biomass & coke gasification, steel mill off gases etc. More specifically the present invention protects the microbes over limitation of operating temperature & residence time outside fermentation process providing energy savings compared to the other available conventional distillation schemes and membrane separation processes. The process is also applicable for Fermentation technologies having limitations on temperature & residence time apart from Gas fermentation Technologies. The system can work for fermentation broth containing organic compounds (i.e. ethanol, propanol, butanol, Acetone, iso-propyl alcohol), especially ethanol, in a concentration as low as 1 wt %.

In accordance with the present invention, broth stream containing ethanol (named as broth solution or fermented broth) is obtained from a gas fermentation facility having live microbes. The fermented broth thus obtained contains around 1-5 wt. % ethanol depending on the gas feed quality while rest is mostly water and other impurities along with live microbes. According to the present invention, ethanol is recovered from the fermented broth at low temperature (i.e. typically below or at 50° C. to protect the live microbes) and the ethanol thus recovered is further purified in downstream distillation and dehydration section to achieve the fuel grade high purity ethanol. In accordance with the present invention, ethanol separation from the broth is achieved effectively using integrated vapor compressing unit (turbofans), evaporator/reboiler and broth stripper column (vacuum distillation system). The distillation of ethanol is performed with column operation under vacuum conditions to achieve low temperature separation ensuring activity of micro-organisms in recycle broth. The vapor compressing unit (turbofan) is used to achieve integration of vacuum column overhead vapor heat to generate stripping steam in the falling film evaporator reboiler. This combination not only gives energy savings but also meet the objective of low temperature separation of ethanol from broth containing live microbes.

According to the main feature, the present invention provides an integrated process for separation of an organic compound from a fermented broth, the process comprising:
(a) feeding a degassed and pre-heated fermented broth into a broth stripper column for generating a vapor;
(b) compressing the vapor obtained from overhead of the broth stripper column in a turbofan to obtain a compressed vapor at a pressure ranging from 160 to 200 mmHg;
(c) routing a demineralized water from bottom of the broth stripper column to a falling film evaporator to obtain stripping steam, wherein the stripping steam is routed into the broth stripper column;
(d) routing the compressed vapor obtained in step (b) to the falling film evaporator for heat transfer from the compressed vapor to the demineralized water for generating the stripping steam, wherein the compressed vapor is condensed to obtain a mixture of a condensed liquid and a remaining vapor;
(e) routing the mixture of the condensed liquid and the remaining vapor obtained in step (d) to a broth stripper condenser for condensing the remaining vapor into a condensed liquid; and
(f) collecting the condensed liquid obtained in step (d) and step (e) in a rectifier feed drum for distillation to obtain 15-25 wt % of the organic compound;
wherein the broth stripper column is operated at temperature ≤50° C. for a residence time of ≤10 minutes;
wherein the organic compound is selected from ethanol, propanol, butanol, acetone and iso-propyl alcohol.

In a preferred embodiment the residence time ranges from 1-10 minutes, more preferably 5-10 minutes and the temperature in the broth stripper column ranges between 15 to 50° C., more preferably 30-45° C.

In an embodiment, the fermented broth further contains living microbes, wherein the fermented broth is produced in different fermentation technologies, especially gas fermentation. Additionally, the fermented broth comprises of enzymes. The process of ethanol separation is thus operated at a low temperature with low residence time to ensure that the micro-organisms remain alive in the process and are further recycled to a fermentation unit.

In a preferred feature, the present invention provides an integrated process for separation of ethanol from a fermented broth, the process comprising:
(a) feeding a degassed and pre-heated fermented broth into a broth stripper column for generating a vapor;
(b) compressing the vapor obtained from overhead of the broth stripper column in a turbofan to obtain a compressed vapor at a pressure ranging from 160 to 200 mmHg;
(c) routing a demineralized water from bottom of the broth stripper column to a falling film evaporator to obtain stripping steam, wherein the stripping steam is routed into the broth stripper column;
(d) routing the compressed vapor obtained in step (b) to the falling film evaporator for heat transfer from the compressed vapor to the demineralized water for generating the stripping steam, wherein the compressed vapor is condensed to obtain a mixture of a condensed liquid and a remaining vapor;
(e) routing the mixture of the condensed liquid and the remaining vapor obtained in step (d) to a broth stripper condenser for condensing the remaining vapor into a condensed liquid; and
(f) collecting the condensed liquid obtained in step (d) and step (e) in a rectifier feed drum for distillation to obtain 15-25 wt % of the ethanol; wherein the broth stripper column is operated at temperature ≤50° C. for a residence time of ≤10 minutes.

The process described in steps (a) to (f) of the present invention is equally applicable for the separation of propanol, butanol, acetone and iso-propyl alcohol (IPA) from the fermented broth In an embodiment, the present invention provides that the fermented broth fed into the broth stripper column comprises 1-5 wt % of the organiccompound, particularly ethanol.

In another embodiment, the present invention provides a broth recycle comprising less than or equal to 0.15 wt % of the organic compound, preferably ethanol, obtained from a side draw of the broth stripper column and recycled from the broth stripper column for fermentation. The broth recycle preferably contains 0.05-0.15 wt % of ethanol, more preferably the broth recycle contains 0.08-0.1 wt % of ethanol.

In a preferred embodiment, the broth stripper column is provided with a packed bed section packed with a mass transfer bed of packing material for operating the broth stripper column under vacuum condition at a pressure ranging from 45 to 60 mm Hg, preferably 56 mm Hg, and a temperature of <45° C. Further, the broth stripper column is provided with chimney trays below the packed bed section for removal of the broth recycle and also provided with an additional tray section at bottom for providing the demineralized water to the falling film evaporator for generation of stripping steam.

In another embodiment, the separation process of the present invention provides that for start-up operation a bottom product from the broth stripper column is heated with a low pressure steam (having a pressure of about 5 bar) in an auxiliary reboiler to generate stripping steam for start-up.

In yet another embodiment, the present invention further provides that during start-up operation of the process, vapor obtained in step (a) (of the process described above) is routed to a start-up condenser to obtain a condensed liquid followed by routing of the condensed liquid to the rectifier feed drum.

Figure 2:
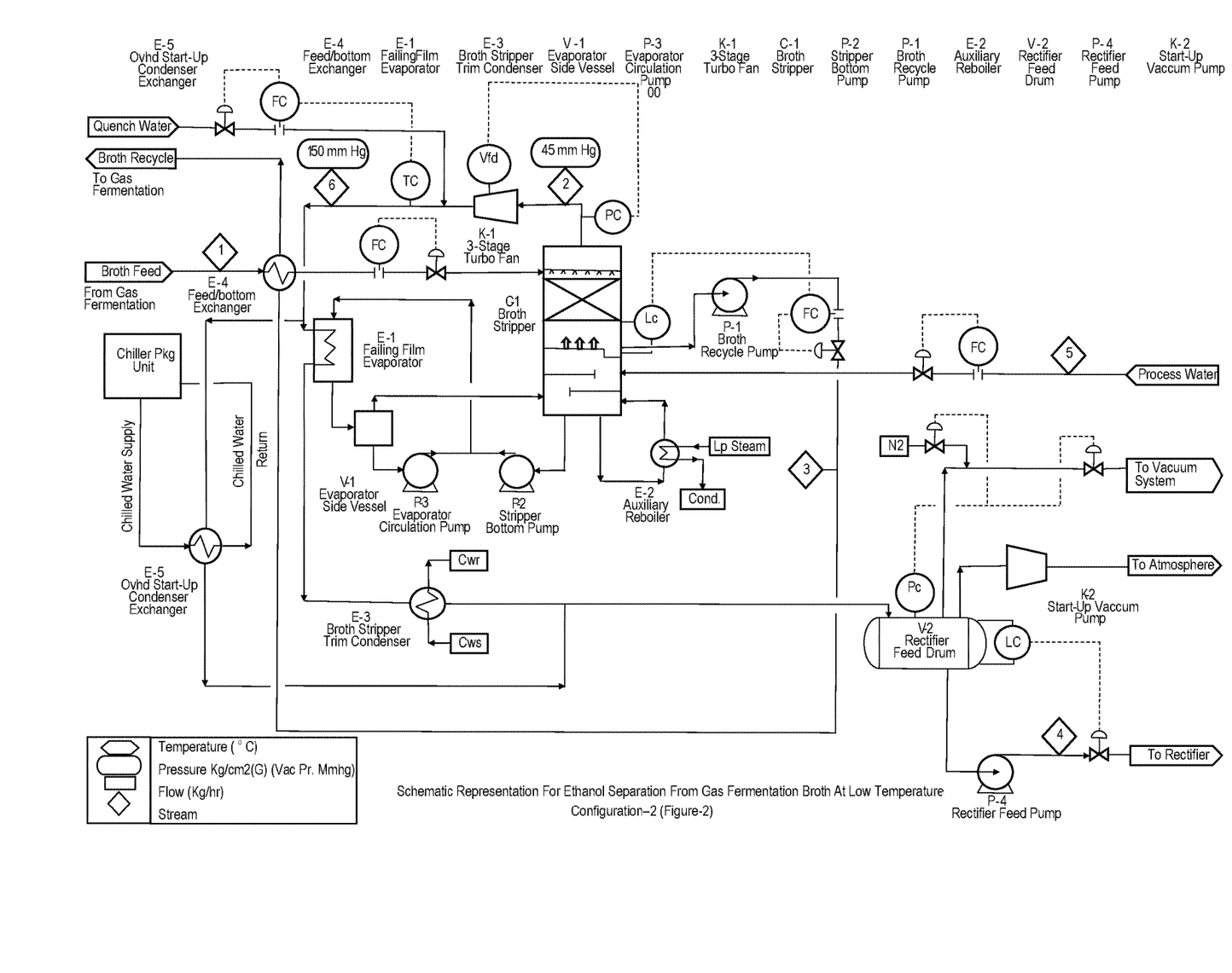
FIG. 2 is a schematic representation of Configuration-2 for Ethanol Recovery from Fermented broth accordance with the present invention (for operating in hot countries).

The start-up operations facilitate the initiation of the process to reach minimum flow requirement of turbofans. Once the process starts running and turbofan comes in opration, the start-up related apparatus are turned off and the process is operated based on the heat generated within the system in an energy saving mode by preserving the energy of the system through efficient heat transfer processes. In hot countries, cooling water temperature is higher resulting in reduced cooling of the overhead vapor. Thus for operating in hot countries, in a preferred embodiment, the start-up condenser optionally uses chilled water to provide a vacuum pressure of 45 mmHg at a temperature ranging from 42° C. to 43° C. in the broth stripper column. Thus, for operating the process in hot countries, the present invention provides a 3-stage turbofan operation for separation of an organic compound, particularly ethanol (FIG. 2).

In a preferred embodiment for the process operating in hot countries, the present invention provides a 2-stage turbofan operation for ethanol separation wherein the broth stripper condenser is optionally provided with a continuous chiller operation to provide a vacuum pressure of 45 mmHg at a temperature ranging from 42° C-43° C. in the broth stripper column thereby eliminating the need of using for an additional start-up condenser in the separation process.

The present invention also provides an integrated system for separation of an organic compound from a fermented broth, wherein the organic compound is selected from ethanol, propanol, butanol, acetone, iso-propyl alcohol, the system comprising:
 a broth stripper column (C-1) provided with a packed bed section packed with a mass transfer bed of packing material, a chimney tray below the packed bed section for removal of a broth recycle, and a tray section at bottom for providing a demineralized water to a falling film evaporator for generation of a stripping steam;
 a turbo fan (K-1) for compressing a vapor obtained from overhead of the broth stripper column (C-1);
 a falling film evaporator (E-1) for heat transfer from a compressed vapor to the demineralized water obtained from the bottom of the broth stripper column (C-1) and to obtain a mixture of a condensed liquid and a remaining vapor;
 a condenser (E-3) for condensing the remaining vapor obtained from the falling film evaporator (E-1) to obtain a condensed liquid;
 a rectifier feed drum (V-2) for collecting the condensed liquid obtained from the condenser (E-3);
 an auxiliary reboiler (E-2) for heating a bottom product from the broth stripper column (C-1) with a low pressure steam during start-up operation; and
 a start-up condenser (E-5) for condensing the compressed vapor during start-up operation.

In a preferred feature, the integrated system is employed for separation of ethanol.

In another embodiment, the system comprises a broth recycle pump (P-1) for receiving a broth recycle from a side draw of the broth stripper column (C-1); wherein the broth recycle comprises less than or equal to 0.15 wt % of the organic compound, preferably ethanol.

In a further embodiment, the system comprises start-up vacuum pump (K-2) at a vapor outlet of the rectifier feed drum (V-2) for maintaining vacuum.

The present invention is operated based on 3 different configurations depending on the cooling water supply temperature in the hot and cold countries. All the 3 configurations are workable in cold countries with configuration 2 and 3 specifically facilitated for hot countries. The illustrative configurations for ethanol are described below:

Configuration 1 (FIG. 1): Integrated Vacuum Column, FFE with Turbofan Configuration (3-satge Turbofans) 30

In this configuration (FIG. 1), broth received from upstream Fermentor after degassing (stream #1) is preheated in (feed/bottom exchanger) and enters to the Vacuum column (C-1) operated under Vacuum. The column is operated with heat integration of Overhead vapors to the Falling Film evaporator reboiler (E-1) to reutilize the heat of overhead vapors and thus reduce the need of any external energy inputs for Stripping Ethanol from Broth.

Figure 1:
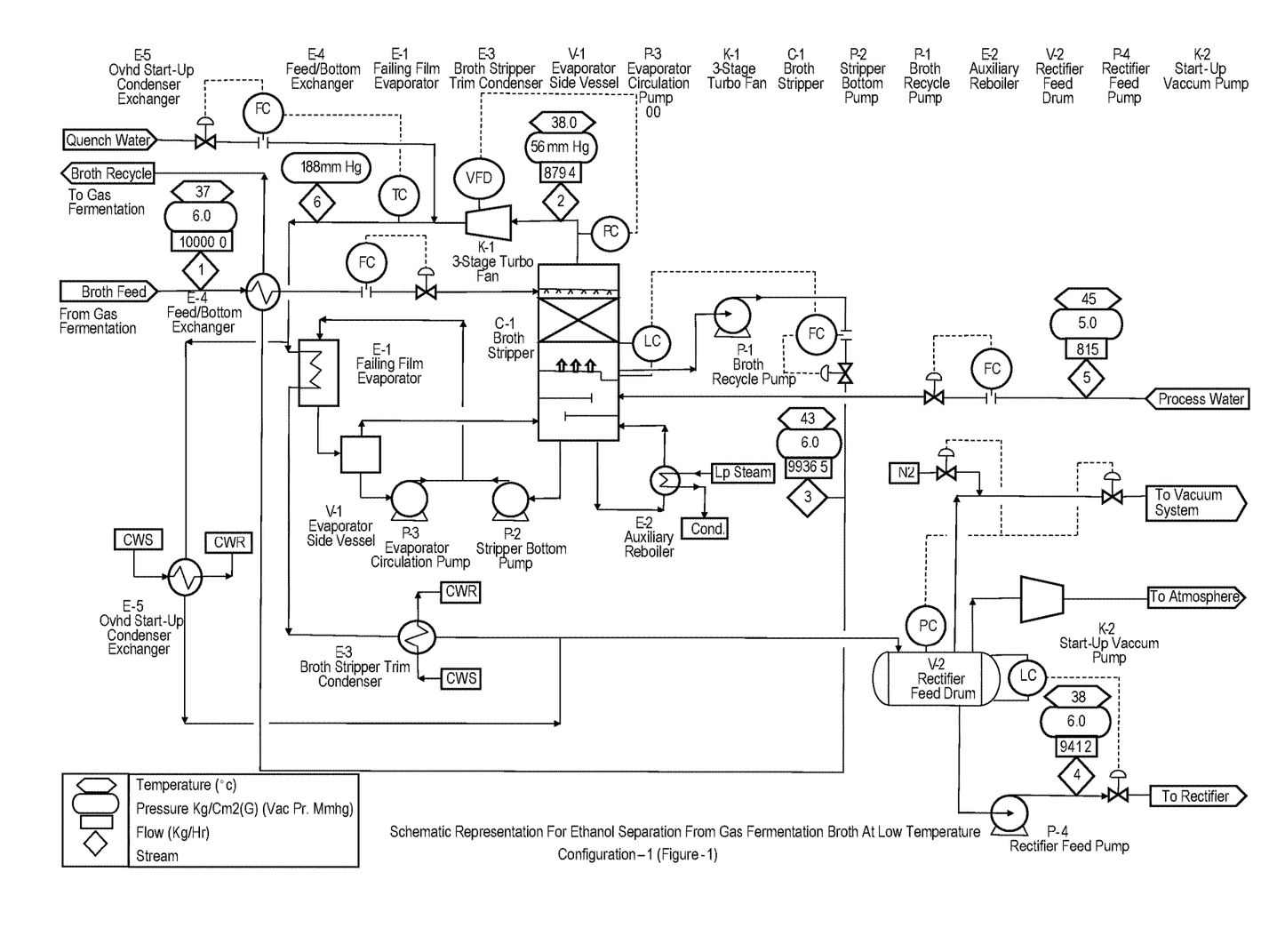
FIG. 1 is a schematic representation of Configuration-1 for Ethanol Recovery from Fermented broth in accordance with the present invention.

Low temperature in the column is maintained with the operation under vacuum condition of ~56 mmHg top pressure and Low Delta P in column is ensured with use of packed bed. The overhead vapors contains 20-22 wt % ethanol (stream #2), and compressed with Turbo fans (K-1) to achieve the pressure sufficient for heat transfer to Falling film evaporator (FFE) reboiler (E-1) (i.e. bottom temperature and FFE temperature approach defines the turbofan outlet pressure). Chimney Tray is installed below the packed beds for the removal of the Broth recycle (stream #3), and bottom section of column contains tray section where process water (stream #5) enters and reaches to FFE for vapor generation. FFE (E-1) tube side outlet vapors enter the bottom tray section of column and acts as stripping media for ethanol separation. While FFE shell outlet vapors+ condensed liquid is further cooled in trim condenser (E-3) and collected in rectifier feed drum (V-2) for processing in downstream distillation section (stream #4). The uncondensed vapor that is left over is further routed to the vacuum scrubber system. Vacuum in the complete system is maintained with Operating Vacuum scrubber & Vacuum pump which is installed at the vapor outlet of Feed surge drum (V-2) downstream of this unit.

For start-up of turbofans (K-1), auxiliary re-boiler (E-2) is provided with LP Steam to achieve the minimum flow requirement of Turbo Fans (K-1). The system vacuum is maintained initially using start-up Vacuum pumps (K-2) and generated steam is condensed with OVHD start-up cooling water condenser (E-5). After getting minimum flow of overhead vapors, Turbofans (K-1) are started and stabilized, then re-boiler duty required for column is available from overhead vapors through FFE Reboiler (E-1).

Through this approach low temperature broth separation is achieved along with heat integration without adversely impacting the growth of live microbes which are the heart of the fermentation process. The piping from Gas-Fermentor to the Distillation section and Back to Fermentor are minimized along with keeping Minimum required volume in the equipment like Degasser, Vacuum Distillation Column to minimize overall residence time for Broth outside of Fermentor.

Configuration 2 (FIG. 2): Integrated Vacuum Column, FFE with Turbofan Configuration (3-Stage Turbofan+Start-up Chillers)

This scheme (FIG. 2) further allows operating the broth separation column at ~42-43° C. with deeper Vacuum of 45 mmHg. Turbofans (K-1) with 3-stage configuration are sufficient for the pressure increase requirement of the column with Heat integration. But during the start-up the deeper vacuum of 45 mmHg requires the start-up Condenser (E-5) operation with chilled water. For low temperature in condenser chiller unit is required with the 3-Stage Turbo Fan configuration. This Configuration is applicable in hot countries where cooling water temperature is higher and limiting the condensing of the vapor. Further this configuration provides significant operating margins over design limitation of Microbes operating temperature (typically <45° C.).

Figure 3:
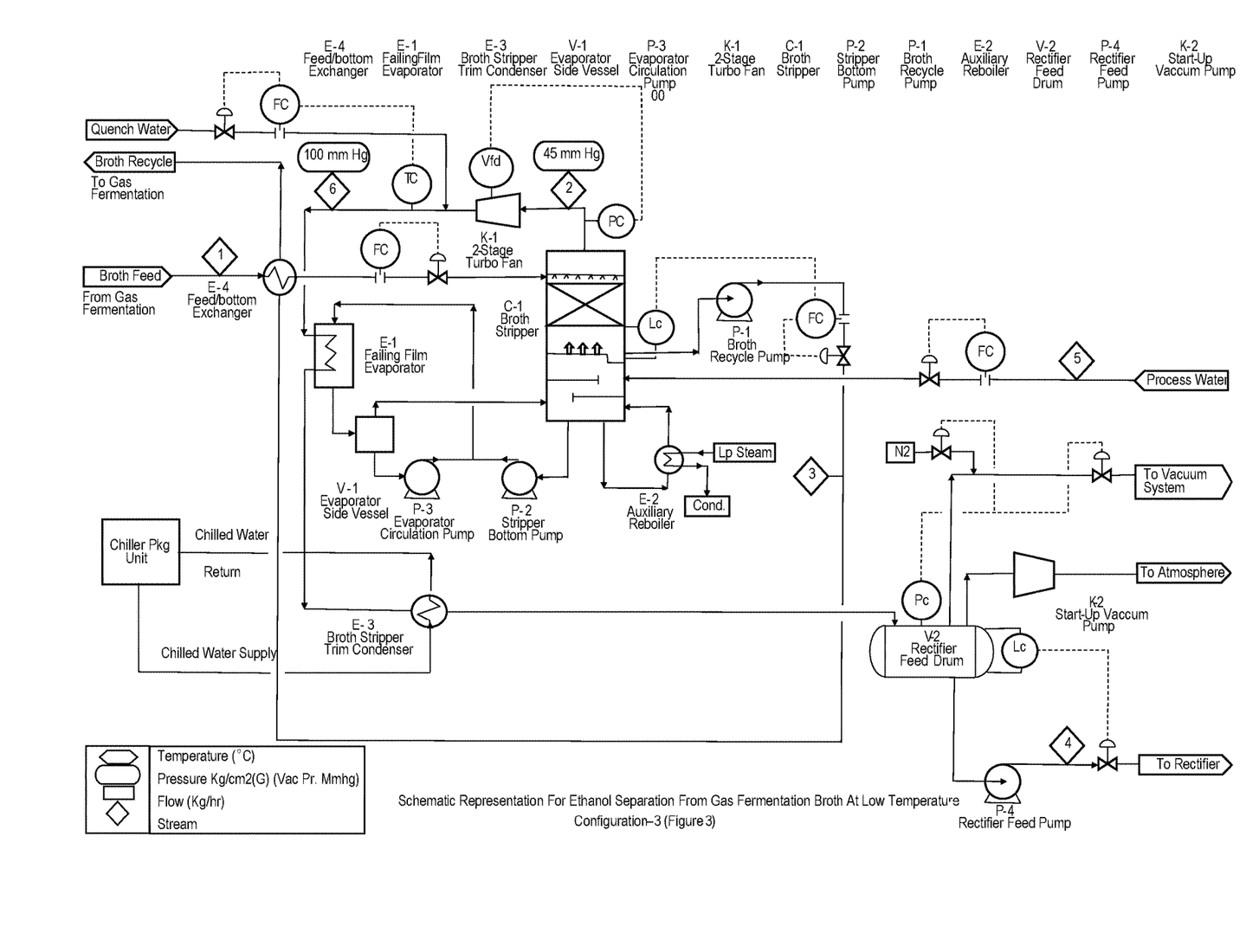
FIG. 3 is a schematic representation of Configuration-3 for Ethanol Recovery from Fermented broth in accordance with the present invention (for operating in hot countries).

Configuration 3 (FIG. 3): Integrated Vacuum Column, FFE with Turbofan Configuration (2-Stage Turbofan+Continuous Operating Chillers)

Vacuum Configuration (as mentioned in configuration 2) with 3-stage turbofan allows the installation of Trim Condenser with cooling water at ~33° C. (i.e. dew point is achieved with cooling water-no chilled water requirement). While, Turbofans with 2-stage (configuration-3) has lower dew point and requires chilled water (i.e. continuous chiller operation). This configuration (FIG. 3) allows Column operation at 45 mmHg and less power in the turbofan with the elimination of one stage. However, there will be net increased power requirement due to chiller operation, but also allows greater margin in column bottom temperature resulting in column operation ~42-43° C.

In accordance with the present invention, the process for ethanol separation from fermentation broth at low temperature (typically <45° C.), makes use of the following major components:
a) Integrated Turbofans (K1), with Falling Film Evaporator (E-1) & Vacuum Distillation System (C-1);
b) Vacuum Distillation Column (C-1) having a mass transfer beds of packing material;
c) Side draw of Broth Recycle Stream with Broth Recycle Pump (P-1) from Vacuum Distillation column (C-1);
d) Start-up Vacuum Pump (K-2) & Start-up Overhead Condenser (E-5);
e) Start-up Auxiliary Reboiler (E-2); and
f) Rectifier Feed Drum (V-2).

In accordance with the present invention, the Integrated Turbofans (K1), Falling Film Evaporator (E-1) & Vacuum Distillation System/Broth stripper column (C-1) are designed in such a way so that the broth recycle having <0.1 wt % of ethanol is obtained in the process ensuring compliance to operating limitation of temperature (typically <45° C.) and residence time (<10 minutes) for broth containing live microbes.

In accordance with the present invention, the process for ethanol separation from broth at low temperature operation discloses the following characteristic features:
a) Feeding the Fermented Broth Feed Ex Fermentor to Broth Stripper Column (C1) operating at pressure of 56 mmHg (Configuration-1, FIG. 1) for temperature typically <45° C. or 45 mmHg (Conf-2 & 3) for temperature <43° C.
b) Overhead vapors from broth stripper(C1) are compressed with Turbofans (K1) to achieve pressure & temperature sufficient for energy/heat transfer to downstream Falling Film Evaporator (E-1)
c) Use of Falling Film Evaporator Reboiler (E-1), which achieves Low temperature approach for the effective heat transfer from Column Overhead Vapor to Column Bottom Water Stream.
d) Use of Packed bed Column instead of tray/grid trays in Broth Stripper (C1) to achieve Low delta P and ensuring operation within temperature limitation at the Broth Collection trays & at the bottom of the column.
e) Installation of Chimney trays under packed bed section of broth stripper column (C1) for collection of the Recycle Broth containing live microbes and recycling of the collected broth back to upstream Fermentor in the fermentation section.
f) Minimum piping and distances between Fermentation Section and Broth
Separation Section to Minimize Broth Circulation and Residence time outside fermentation area.
g) Installation of small tray section below chimney tray for the stripping steam generation through FFE (E-1).
h) Installation of Auxiliary Re-boiler (E-2) with low pressure (LP) steam for the start-up operation to achieve turbofan (K-1) minimum flow requirement.
i) Installation of Vacuum system for creating and maintaining the Vacuum conditions during start-up and continuous operation.
j) Operation of Column along with chiller system for overhead vapors for start-up in configuration-2 (FIG. 2) and continuous operation in configuration-3 (FIG. 3) in case of Cooling water temperature limitation in hot countries.

The process protects the live-microbes (bio-catalyst), meets the maximum temperature limitation (typically <45° C.) & residence time criteria (<10 minutes) required for the ethanol separation from fermented broth for the technology.

Figure 4:
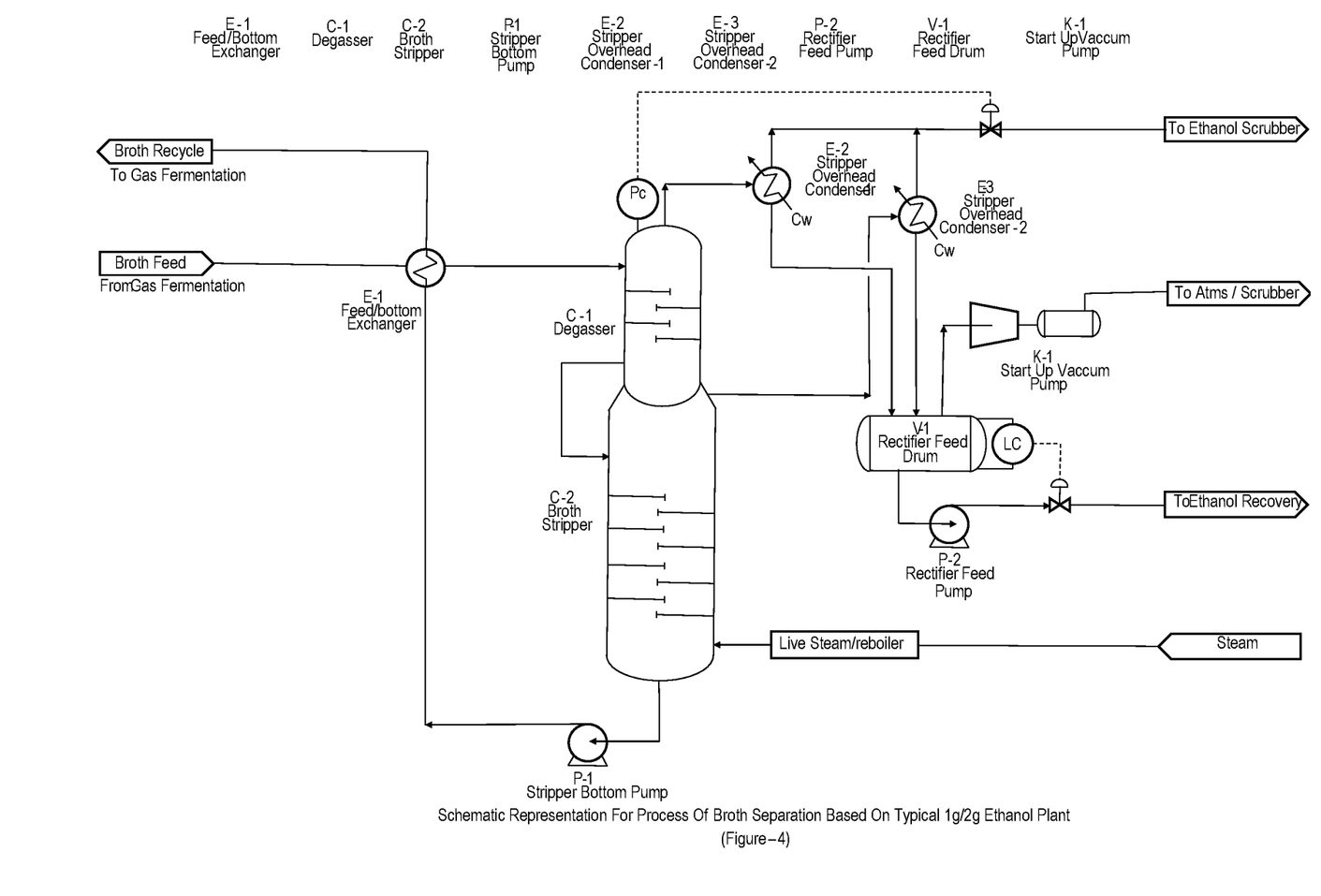
FIG. 4 is a schematic representation of the process for broth separation based on typical 1G/2G ethanol plant

FIG. 4 illustrates the schematic representation of conventional method of ethanol separation, if adopted for Gas Fermentation Broth Separation. This type of scheme is adopted in conventional 1st & 2nd Generation technologies mainly for production of ethanol from Molasses, rice husk, wheat straw, etc. Since conventional 1G/2G technology are not based on the recycling of the live micro-organisms, so the ethanol separation can be performed at the distillation column bottom of temperature ~90° C. or above using Low Pressure steam reboiler/direct injection. Overhead Vapors (20-22 wt % ethanol rich) are condensed and further routed to the downstream Ethanol recovery & Dehydration section for getting High Purity Ethanol. Such type of convectional schemes cannot work for the processes utilizing Bio-Catalyst (live Microbes) for fermentation processes. Such high temperatures will lead to killing of the microbes and reduce Growth/activity of microbes in the gas/bio-mass fermentation processes in upstream Fermentor.

Figure 5:
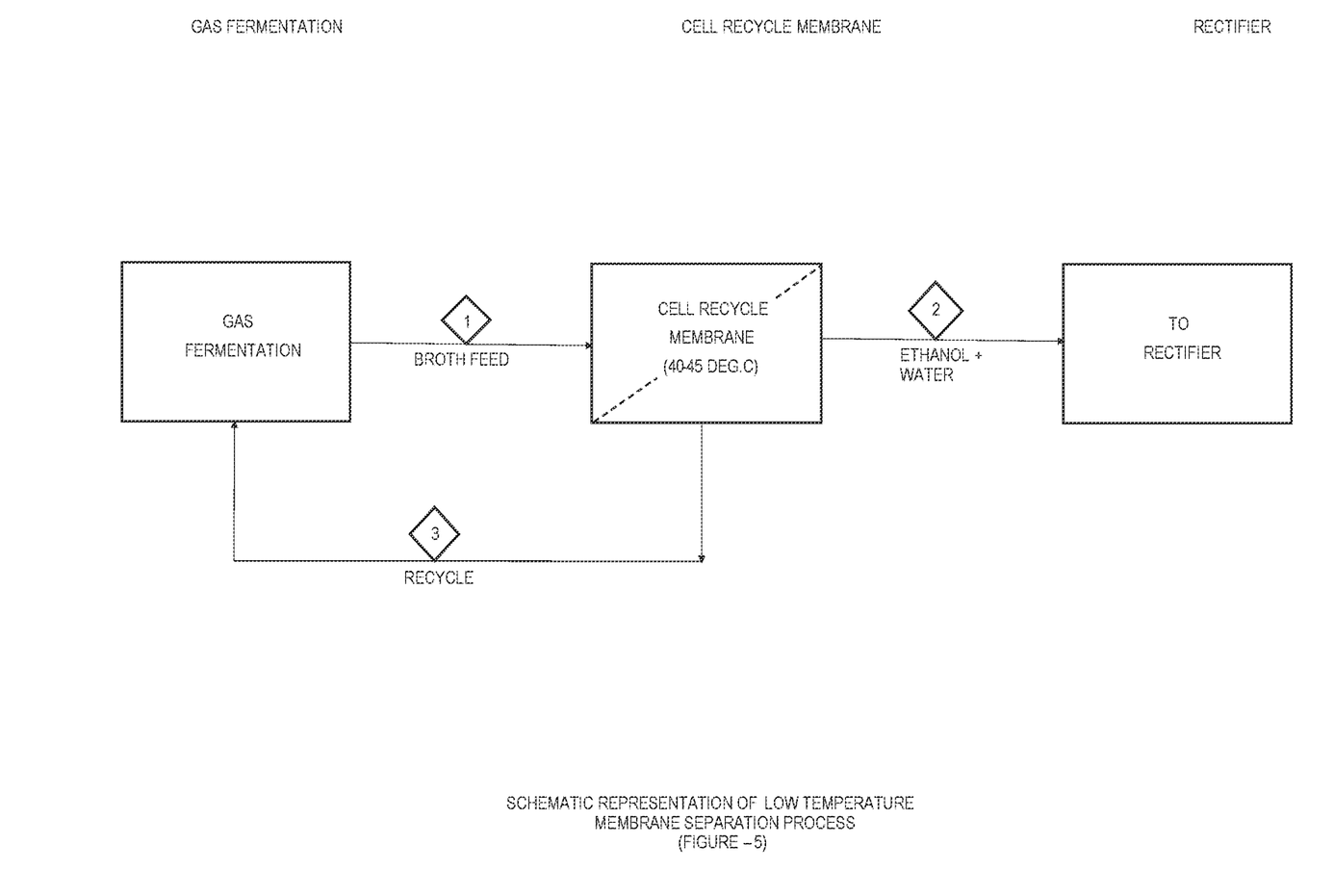
FIG. 5 illustrates a schematic of Membrane Separation Methods for ethanol recovery from Fermented broth.

Again, FIG. 5 illustrates a schematic representation of membrane separation methods for ethanol recovery from fermented broth. In such system, a cell recycle membrane is used for separating the ethanol-water mixture from broth containing live microbes and allowing the micro-organism to recycle back to fermentation process with the low temperature requirement. However, repair & maintenance costs are high for membrane separation modules. Also, very large area is required for installing such membranes especially for lower growth rate of microbes depending on the feed gas constituents.

Further, the reliability of membranes are poor w.r.t changes in operating condition, feed quality and any ingress of particulate matter in broth and the lower life cycle of the membranes require frequent replacement during the project life.

The disclosed process of separation of the organic compound (i.e. ethanol, propanol, butanol, Acetone, iso-propyl alcohol), preferably ethanol from the fermented broth provides the following technical advantages:

- Low temperature separation & recovery of ethanol from the fermented broth containing live microbes typically below or at 50° C.
- The activity of the microbes is ensured by maintaining the residence time of the microbe containing broth outside the Fermentor<10 mins.
- Applications with integrated Turbofans, evaporator and vacuum distillation system for energy optimization and lowering the OPEX (Operating Cost).
- No external steam input is required apart from the start-up operation.
- Approximately power reduction of 40-50% can be achieved compared to conventional scheme.
- Approximately 60-70% reduction in cooling water can be achieved compared to conventional scheme.
- This process is also applicable for other Fermentation technologies having limitations on temperature & residence time in addition to the mentioned Gas fermentation Technologies.
- This process can work for fermentation broth ethanol concentration as low as 1 wt %.

Having described the basic aspects of the present invention, the following non-limiting examples illustrate specific embodiment thereof.

Configuration 1 receives Broth Feed from Gas fermentation section with 2-3 wt % Ethanol and which is enriched to 20-22 wt % Ethanol using this integrated Turbofans, Falling Film Evaporator and Vacuum Distillation System. The Broth Stripper is operated 56 mmHg to keep column bottom (broth recycle) temperature typically <45° C. Results are summarized in Table-1

TABLE 1

Ethanol separation achieved using Configuration 1

| | Stream | | | | |
|---|---|---|---|---|---|
| | 1 Broth Feed Ex Fermentor | 2 Broth Stripper OVHD Vapor | 3 Broth Recycle | 4 Feed to Rectifier | 5 Process Recycle Water |
| Flow (Kg/Hr) | 100000 | 8794 | 99365 | 9412 | 8159 |
| Temp (C.) | 37 | 38 | 43 | 38 | 45 |
| Pressure, (Kg/cm$^2$g/mmHg) | 6.0 | 56 mmHg | 6.0 | 6.0 | 5.0 |
| Ethanol (wt %) | 2-3% | 20-22% | <0.1% | 20-22% | NIL |

Expected major benefits with the integrated process of ethanol separation disclosed in the present invention as per configuration-1 (FIG. 1) with respect to the typical conventional process as described in FIG. 4 is summarized in Table-4

TABLE 2

Comparison of the conventional process and the proposed invention in the illustration for ethanol separation

| S. No. | Parameter | Conventional process* | Present Process |
|---|---|---|---|
| 1 | Broth Feed Capacity (kg/hr) | 100000 | 100000 |
| 2 | Feed Ethanol (wt %) | 2-3% | 2-3% |
| 3 | Enriched Ethanol (wt %) | 20-22% | 20-22% |
| 4 | Ethanol wt % in Recycle Broth Stream (return stream to Fermentor) | <0.1% | <0.1% |
| 5 | Vacuum Stripper Top Pressure | 56 mmHg | 56 mmHg |
| 6 | Steam Requirement (T/Hr) | 10-12 | NIL |
| 7 | Power requirement (MW) | 1.4-1.6 (for chilled water system) | 0.7-0.8 (for turbofans) |
| 8 | Cooling Water (m$^3$/hr) | 1500-1700 (for chilled water system) | 500-600 (for trim condenser) |

*Conventional process with chilled water system, wherein chilled water is required to condense overhead vapors from vacuum column.

Conventional process requires reboiler with the LP steam on continuous basis. Accordingly as shown in the above Table 2, the energy required for the recovery of 20-22 wt % ethanol from the fermented feed having 2-3 wt % ethanol, will be equivalent to 10-12 tons/hr of LP steam in case of the conventional process, while in the proposed invention steam is not required for continuous operation of Broth stripper. In conventional process, for the condensation of the Broth stripper overhead vapors at 56 mmHg, chilled water system is required due to low dew point of the generated vapors at the operating condition which in turn requires 1.4-1.6 MW of power and 1500-1700 m$^3$/hr of cooling water for the circulating chilled water system. In contrast, the proposed process of ethanol separation requires only 0.7-0.8 MW of power for the turbofan operation and 500-600 m$^3$/hr of cooling water for the trim condenser.

The invention claimed is:

1. An integrated process for separation of an organic compound from a fermented broth, the process comprising:
   (a) feeding a degassed and pre-heated fermented broth into a broth stripper column for generating overhead vapors, wherein the broth stripper column is operated at a temperature ranging from 15 to 50° C. for a residence time ranging from 1-10 minutes;
   (b) compressing the overhead vapors obtained from an overhead of the broth stripper column with a turbofan to obtain compressed vapors at a pressure ranging from 160 to 200 mmHg;
   (c) routing demineralized water from a bottom of the broth stripper column to a falling film evaporator;
   (d) routing the compressed vapors obtained in step (b) to the falling film evaporator for heat transfer from the compressed vapors to the demineralized water for generating a stripping steam, wherein the compressed vapors are condensed to obtain a mixture of a condensed liquid and remaining vapors and wherein the stripping steam generated is routed into the broth stripper column;
   (e) routing the mixture of the condensed liquid and the remaining vapors obtained in step (d) to a broth stripper condenser for condensing the remaining vapors into a condensed liquid; and (f) collecting the condensed liquid obtained in step (d) and step (e) having 15-25 wt. % of the organic compound in a rectifier feed drum; and wherein the organic compound is selected from ethanol, propanol, butanol, acetone and iso-propyl alcohol.

2. The process as claimed in claim 1, wherein the fermented broth fed into the broth stripper column comprises 1-5 wt % of the organic compound.

3. The process as claimed in claim 1, wherein a broth recycle comprising less than or equal to 0.15 wt % of the organic compound is obtained from a side draw of the broth stripper column and is recycled from the broth stripper column for fermentation.

4. The process as claimed in claim 3, wherein the broth stripper column is provided with a packed bed section packed with a mass transfer bed of packing material enabling the broth stripper column to operate under a vacuum at a pressure ranging from 45-60 mmHg, and wherein the broth stripper column is provided with a chimney tray below the packed bed section for removal of the broth recycle.

5. The process as claimed in claim 1, wherein the broth stripper column is provided with a tray section at the bottom for providing the demineralized water to the falling film evaporator for generating the stripping steam.

6. The process as claimed in claim 1, wherein for a start-up operation a bottom product from the broth stripper column is heated with a low pressure steam of 5 bar in an auxiliary reboiler to generate a stripping steam for the start-up operation.

7. The process as claimed in claim 1, wherein for a start-up operation the compressed vapors obtained in step (b) are routed to a start-up condenser to obtain a condensed liquid followed by routing of the condensed liquid to the rectifier feed drum.

8. The process as claimed in claim 7, wherein the start-up condenser comprises a chiller package unit to provide a vacuum pressure of 45 mmHg at a temperature ranging from 42° C. to 43° C. in the broth stripper column.

* * * * *